(12) United States Patent
Attolino et al.

(10) Patent No.: US 8,802,155 B1
(45) Date of Patent: Aug. 12, 2014

(54) IMINOSUGAR IN CRYSTALLINE FORM

(71) Applicant: Dipharma Francis S.r.l., Baranzate (IT)

(72) Inventors: Emanuele Attolino, Palagiano (IT); Andrea Malvestiti, Mapello (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 14/149,022

(22) Filed: Jan. 7, 2014

(30) Foreign Application Priority Data

Jan. 22, 2013 (IT) .............................. MI2013A0083

(51) Int. Cl.
*A61K 9/14* (2006.01)

(52) U.S. Cl.
USPC ........................................................ 424/489

(58) Field of Classification Search
None
See application file for complete search history.

(56) References Cited

U.S. PATENT DOCUMENTS 4,639,436 A 1/1987 Junge et al.

FOREIGN PATENT DOCUMENTS

EP 367748 A2 5/1990

OTHER PUBLICATIONS

Ellen W. Baxter et al., "Expeditious Synthesis of Azasugars by the Double Reductive Amination of Dicarbonyl Sugars", J. Org. Chem., 1994, 59, pp. 3175-3185.
Carlos R. R. Matos et al: "Synthesis of 1-Deoxynojirimycin and N-Butyl-1-deoxynojirimycin", Synthesis, vol. 1999, No. 04, Apr. 1, 1999, pp. 571-573.
Scaros Mike G et al: "A new and improved synthesis of N-butyl-1-deoxynojirimycin", Chemical Industries, New York, NY, US, vol. 53, Jan. 1, 1994, pp. 41-48.
Zhen-Xing Zhang et al: "Facile and stereo-controlled synthesis of 2-deoxynojirimycin, Miglustat and Miglitol", Tetrahedron Letters, vol. 52, No. 29, Jul. 1, 2011, pp. 3802-3804.
Search Report and Written Opinion for the corresponding patent applcation MI 2013A 000083 dated Jun. 24, 2013, 8 pgs.
U.S. Appl. No. 14/097,398, filed Dec. 5, 2013, Emanuele Attolino et al.

*Primary Examiner* — Janet L Andres
*Assistant Examiner* — Timothy R Rozof
(74) *Attorney, Agent, or Firm* — Rothwell, Figg, Ernst & Manbeck, P.C.

(57) ABSTRACT

Iminosugar, which possesses known activity as a glycosyltransferase inhibitor, and is used, for example, in the treatment of Gaucher's disease, in crystalline form, a process for its preparation and a pharmaceutical composition thereof.

11 Claims, 4 Drawing Sheets

IMINOSUGAR IN CRYSTALLINE FORM

Figure 1:
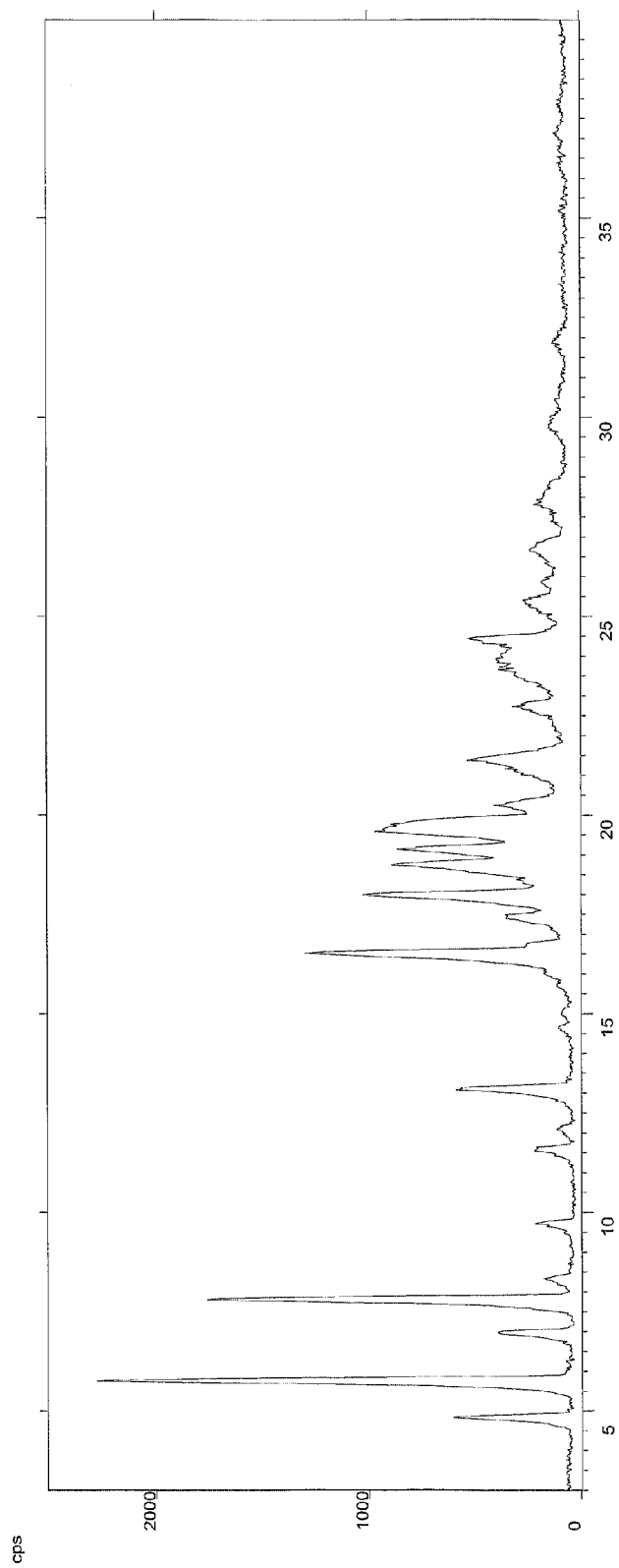

The present invention relates to a glycosyltransferase-inhibiting iminosugar in crystalline form, useful in the treatment of Gaucher's disease, a process for its preparation and a pharmaceutical composition thereof.

PRIOR ART

N-butyl 1,5-dideoxy-1,5-imino-D-glucitol of formula (I), also known as N-butyl 1-deoxynojirimycin or miglustat, is a potent glycosyltransferase inhibitor, and is primarily used in the treatment of Gaucher's disease.

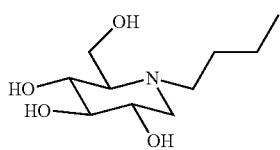

Miglustat belongs to the class of azasugars or iminosugars, namely compounds with multiple biological activities characterised by the presence of a nitrogen atom on the furanose or pyranose ring of the sugar instead of an oxygen atom. The synthesis of azasugars as carbohydrate mimics began over 50 years ago. The first azasugar was synthesised more than forty years ago, and was 1-deoxynojirimycin of formula (II), which was only isolated from natural sources years later, and demonstrated its enormous biological activity.

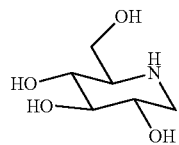

In the 1980s, a number of studies carried out on the biological activity of N-alkylated derivatives of 1-deoxynojirimycin of formula (II) demonstrated that said compounds possess a greater activity than 1-deoxynojirimycin, and the N-butyl derivative of formula (I) proved to be one of the best. As it was a synthetic derivative of 1-deoxynojirimycin, the first syntheses of miglustat were obviously carried out by introducing the butyl chain onto 1-deoxynojirimycin of formula (II) or derivatives thereof with the functional groups protected, by reductive amination with butyraldehyde (see, for example, U.S. Pat. No. 4,639,436 and EP 367748).

Said syntheses obviously shifted the synthesis problem of preparation of the N-alkylated derivative to the efficient synthesis of 1-deoxynojirimycin which, though present in nature in numerous plants and micro-organisms, cannot be extracted in sufficient quantities to allow its industrial exploitation, but must be prepared by chemical synthesis. Various methods of preparation of 1-deoxynojirimycin have been reported over the years, some of them completely chemical or biochemical, with the aid of more or less complex micro-organisms, normally starting with sugars such as glucose and ribose. An interesting synthesis of N-alkylated derivatives of 1-deoxynojirimycin, including miglustat, was published by Baxter and Reitz in *J. Org. Chem.* 1994, 59, 3175-3185. This synthesis uses one of the classic methods of preparing piperidine and pyrrolidine, namely double reductive amination of 1,5-dicarbonyl derivatives with primary amines.

There are three main problems associated with development on an industrial scale of the Baxter and Reitz process, which relate to: 1) the preparation of 5-keto glucose, which involves a number of synthesis steps, the use of compounds based on tin, and low yields; 2) the stereochemistry of the reductive amination, which is selective to give the isomer with gluco stereochemistry only with some types of substituents on the hydroxyls of the starting dicarbonyl; and last but not least 3) the critical steps concerning the handling and purification of the end product, which is purified by flash chromatography.

The first two problems have been partly overcome over the years by the synthesis reported by Matos C. R. R. et al. (*Synthesis* 1999, 571-573), which uses the protected intermediate of miglustat of formula (III)

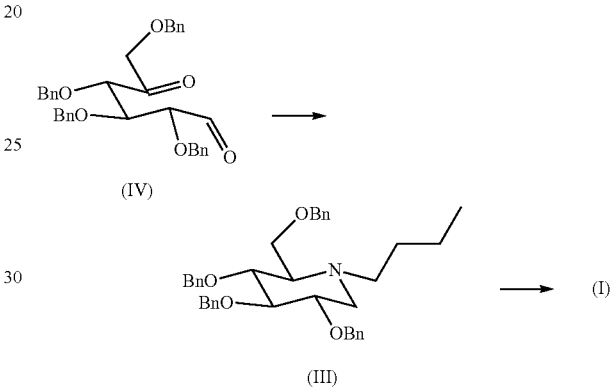

obtained from the protected dicarbonyl of formula (IV), which can be prepared without the use of tin derivatives and with good yields, starting with the commercially available 2,3,4,6-tetra-O-benzyl-D-glucitol, or by reduction of 2,3,4,6-tetra-O-benzyl-D-glucose, also commercially available, which, in turn, can be prepared from D-glucose by known methods. The intermediate of formula (III), after the debenzylation reaction, provides miglustat of formula (I).

The reductive amination reaction of a compound of formula (IV) described above was repeated in our laboratories, and the end-of-reaction crude product was analysed by HPLC.

It was thus demonstrated that in reality, reductive amination is not completely selective, and the formation of the diastereoisomer with the ido configuration of formula (V)

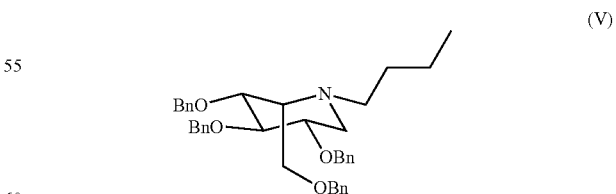

takes place together with that of the desired derivative with the gluco configuration of formula (III).

As reported by Matos C. R. R. et al., the intermediate of formula (III) is purified by flash chromatography on silica gel, and after evaporation of the fractions containing the product, a solid with a melting point of 64-65° C. is obtained.

When the process was repeated, and the resulting solid of formula (III) was analysed, it proved insufficiently pure on HPLC analysis, and the solid was amorphous, with a melting point around 64° C.

There is consequently a need for a more advantageous alternative method of preparing miglustat, and in particular its protected intermediate of formula (III). Said novel method should in particular be more industrially scalable, and therefore include an efficient method of purifying intermediate (III), not involving chromatographic purification, to obtain miglustat with a purity sufficient to allow its use in the pharmaceutical field, and at the same time provide the desired compounds with high yields.

BRIEF DESCRIPTION OF FIGURES AND ANALYSIS METHODS

The X-ray diffraction spectra (XRPD) for N-butyl 2,3,4,6-tetra-O-benzyl-1,5-dideoxy-1,5-imino-D-glucitol of formula (III), in crystalline form, designated here as Form A, and for N-butyl 1,5-dideoxy-1,5-imino-D-glucitol of formula I, here designated as crystalline form I, were collected with the APD-2000 automatic powder diffractometer manufactured by Ital-Structures, under the following operating conditions: Bragg-Brentano geometry, CuKa radiation ($\lambda$=1.54 Å), scanning with a 2θ angle range of 3-40°, with a step size of 0.03° for 1 sec. The detector used is a scintillator.

The DSC thermograms for N-butyl 2,3,4,6-tetra-O-benzyl-1,5-dideoxy-1,5-imino-D-glucitol of formula (III), in crystalline form, designated here as Form A, were acquired with a Mettler-Toledo DSC 822e differential scanning calorimeter, under the following operating conditions: open aluminium capsule, range 30-400° C. at the rate of 10° C./min, with nitrogen as purge gas (80 ml/min).

The DSC thermograms for N-butyl 1,5-dideoxy-1,5-imino-D-glucitol of formula (I), designated here as crystalline form I, were acquired with a Mettler-Toledo DSC 822e differential scanning calorimeter, under the following operating conditions: perforated aluminium capsule, range 30-300° C. at the rate of 10° C./min, with nitrogen as purge gas (80 ml/min).

The water content of N-butyl 2,3,4,6-tetra-O-benzyl-1,5-dideoxy-1,5-imino-D-glucitol in crystalline form, designated here as Form A, was determined by titration using the Karl Fisher technique.

FIG. 1: XRPD spectrum of N-butyl 2,3,4,6-tetra-O-benzyl-1,5-dideoxy-1,5-imino-D-glucitol in crystalline form, designated here as Form A; wherein the main peaks (expressed in ° in 2θ) are found at 4.83, 5.76, 6.96, 7.80, 13.08, 16.50, 17.97, 18.75, 19.14, 19.62±0.2°.

Figure 2:
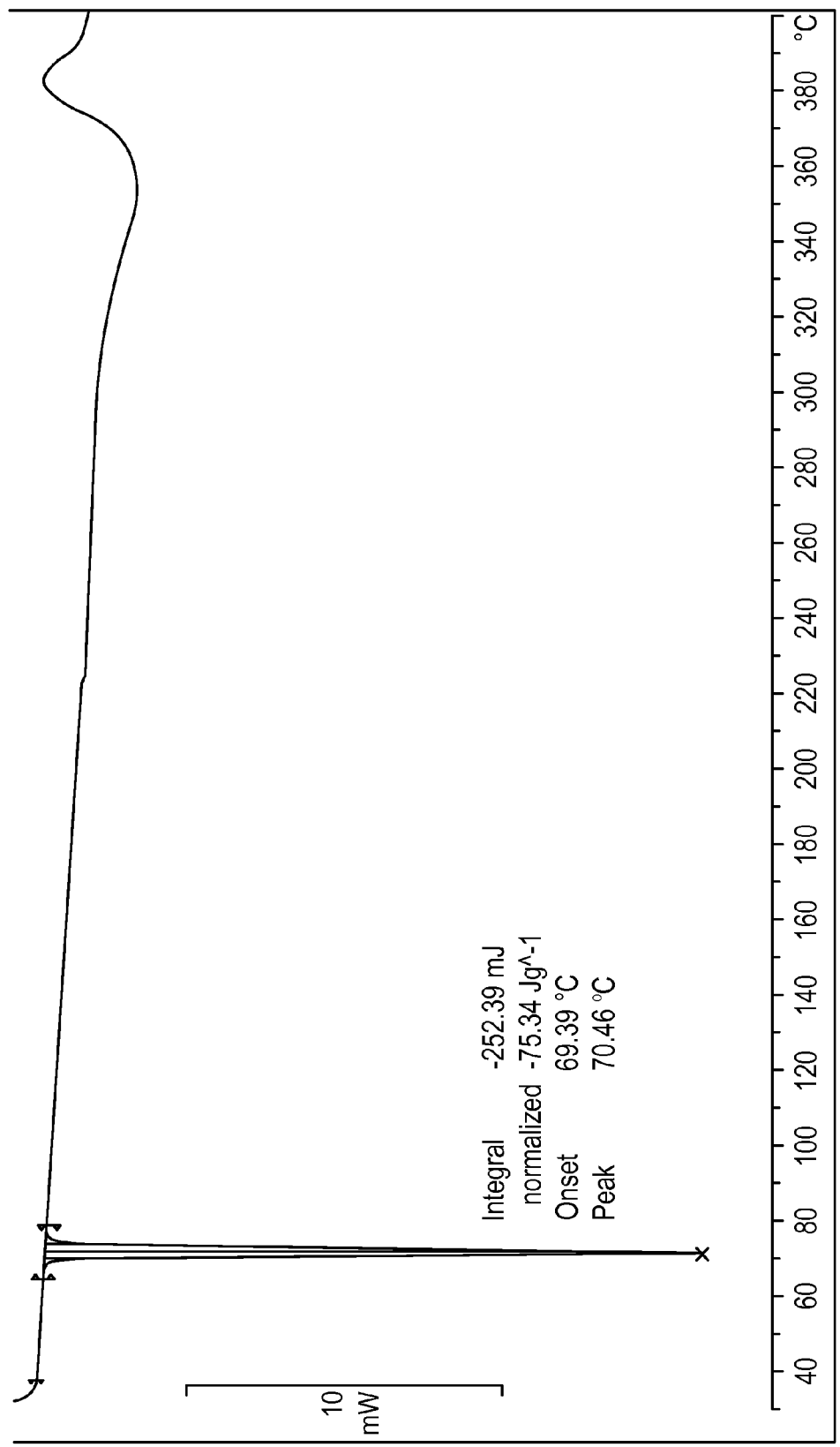

FIG. 2: DSC thermogram of N-butyl 2,3,4,6-tetra-O-benzyl-1,5-dideoxy-1,5-imino-D-glucitol in crystalline form, designated here as Form A. The endothermic peak at about 70° C. indicates the fusion process.

Figure 3:
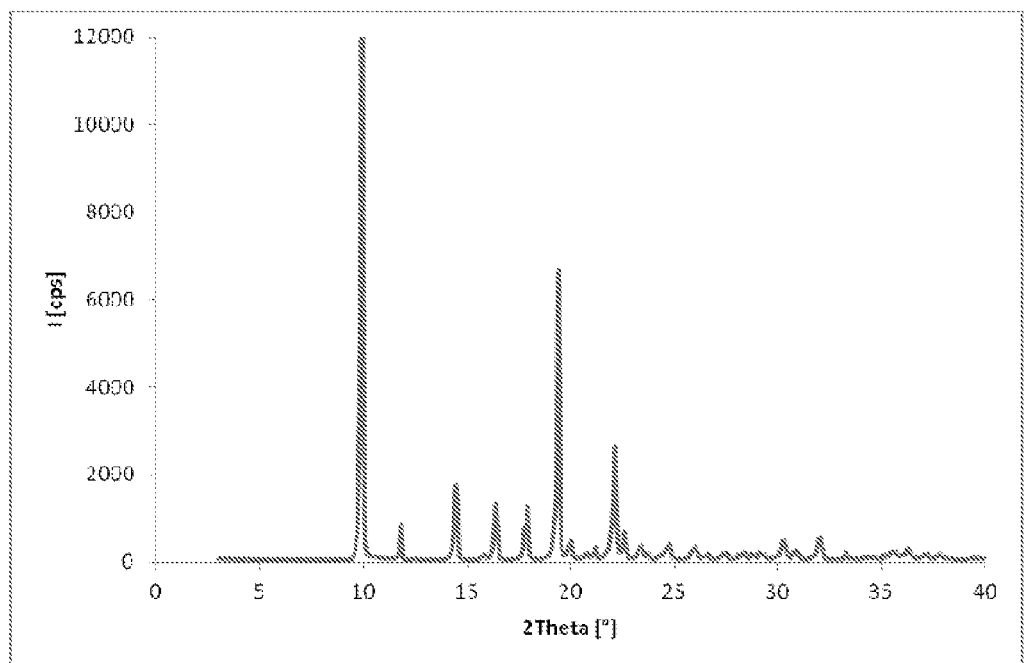

FIG. 3: XRPD spectrum of N-butyl 1,5-dideoxy-1,5-imino-D-glucitol in crystalline form, designated here as Form I; wherein the main peaks (expressed in) 2θ° are found at 9.93, 11.82, 14.46, 15.84, 16.41, 17.76, 17.94, 19.41, 20.01, 20.79, 21.21, 22.14, 22.62, 23.40, 24.75, 26.04 and 30.27±0.2° in 2θ.

Figure 4:
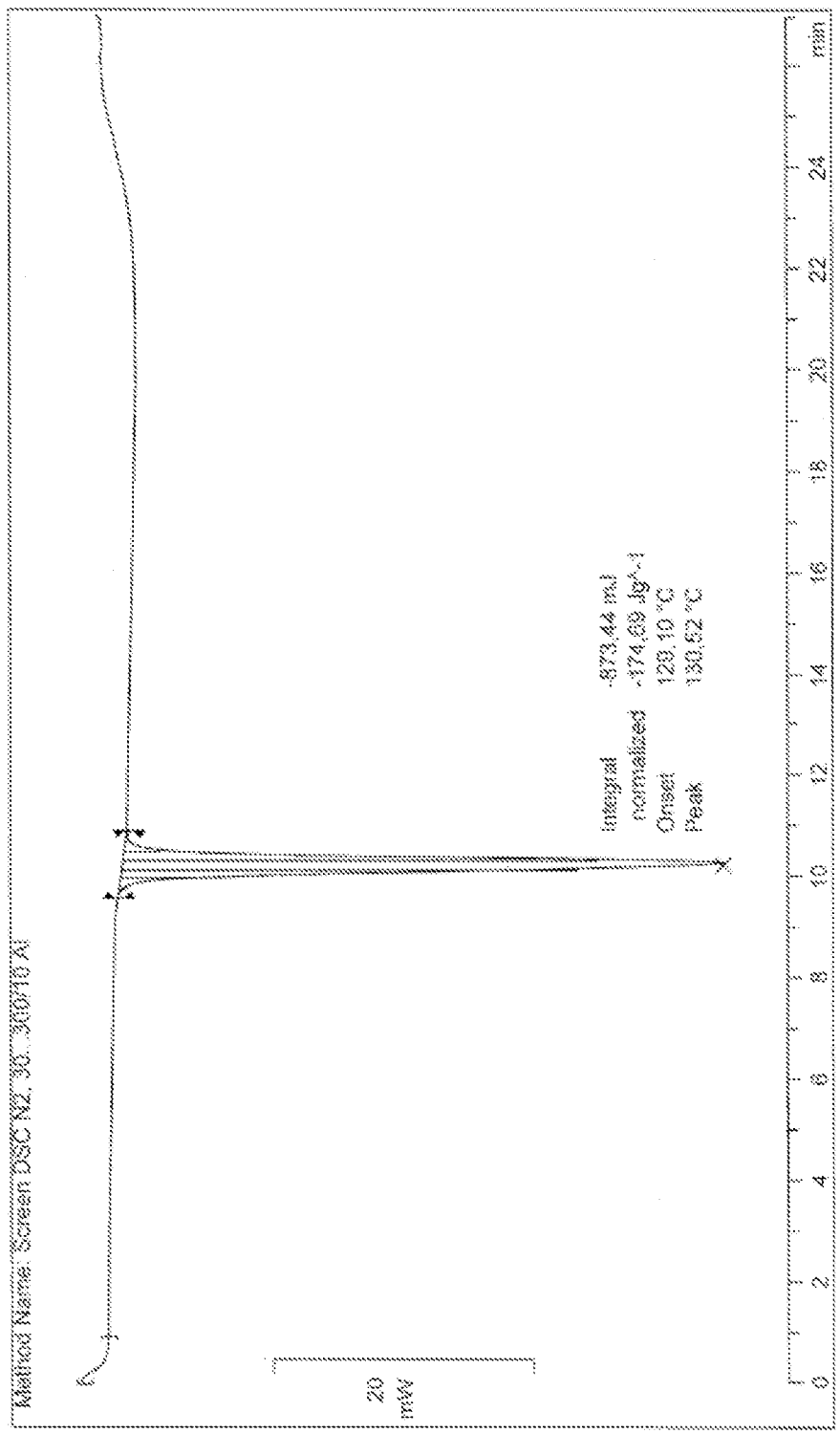

FIG. 4: DSC thermogram of N-butyl 1,5-dideoxy-1,5-imino-D-glucitol in crystalline form, designated here as Form I. The endothermic peak at 129-130° C. indicates the fusion process.

SUMMARY OF THE INVENTION

The invention provides N-butyl 1,5-dideoxy-1,5-imino-d-glucitol in crystalline form, designated here as Form I, a process for its preparation and a pharmaceutical composition thereof.

DETAILED DESCRIPTION OF THE INVENTION

The first subject of the invention is a process for the purification of a compound of formula (III), namely N-butyl 2,3,4,6-tetra-O-benzyl-1,5-dideoxy-1,5-imino-D-glucitol, in the form of a crystalline solid, comprising

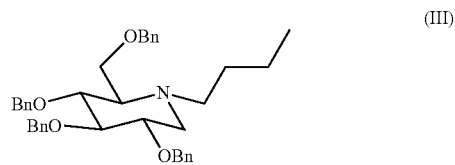 [SMILES: CCCCN1CC(OCc2ccccc2)C(OCc2ccccc2)C(OCc2ccccc2)C1COCc1ccccc1]

its crystallisation from a solvent medium containing a protic solvent.

According to a preferred aspect, said purification process comprises:
- dissolution of a compound of formula (III) in a solvent medium containing a protic solvent,
- the formation of a precipitate; and
- the recovery of the crystalline solid.

The purified product, obtainable by the purification method according to the invention, is a solid in crystalline form of N-butyl 2,3,4,6-tetra-O-benzyl-1,5-dideoxy-1,5-imino-D-glucitol, in particular in the form denominated here as Form A.

A protic solvent, in a solvent medium, can be a straight or branched $C_1$-$C_5$ alkanol, such as methanol, ethanol or isopropanol, typically isopropanol; a carboxylic acid, such as acetic acid; water; or a mixture of two or more, typically two or three, of said solvents.

The concentration of a compound of formula (III) in the starting dispersion can range between about 2 and 90% w/w, preferably between about 30 and 70%.

If necessary, to promote the dissolution of the compound of formula (III), the dispersion containing said compound can be heated until complete dissolution.

The formation of the precipitate can be obtained by maintaining the solution under stirring, for example for a time ranging between about 5 and 20 hours. If necessary, to promote the formation of the precipitate the solution can be cooled, for example to a temperature ranging from about −5° and 5° C. Furthermore, to promote the formation of the precipitate, previously obtained crystals of crystalline form A can also be seeded.

The crystalline solid can be recovered by known techniques, such as filtration or centrifugation. In particular, if necessary, recovery can be promoted by optional addition of a solvent suitable to fluidify the dispersion, such as a $C_1$-$C_5$ alkanol, equal to or different from the one present in the solvent medium.

The solid can then be dried by known methods, for example stove-dried at a temperature ranging between about 30° C. and 55° C., under vacuum.

The crude starting material, to be subjected to the purification method according to the invention, can be a crude compound of formula (III) prepared by any of the known methods reported in the literature, for example as reported by Matos C. R. R. et al. in *Synthesis* 1999, 571-573.

A crude compound of formula (III) used as starting material therefore typically has an assay value ranging between about 10 and 90% w/w, preferably between about 30% and 70% w/w.

The solid in crystalline form of a compound (III), herein denominated Form A, obtainable by the purification method according to the invention, has an XRPD as illustrated in FIG. 1, wherein the most intense peaks (expressed in 2θ°) are found at 4.83, 5.76, 6.96, 7.80, 13.08, 16.50, 17.97, 18.75, 19.14, 19.62±0.2°. It also presents a DSC thermogram as illustrated in FIG. 2, wherein the endothermic peak at about 70° C. indicates the fusion process. As said crystalline form A has a water content lower than 0.2%, preferably lower than 0.1%, it can be defined as essentially anhydrous.

A further subject of the invention is therefore a compound of formula (III), namely N-butyl 2,3,4,6-tetra-O-benzyl-1,5-dideoxy-1,5-imino-D-glucitol, in crystalline form, in particular in crystalline form A as defined above.

The dimension of the crystals of a compound (III) in crystalline form A, as obtainable by the process described above, is characterised by a $D_{50}$ value ranging between about 25 and 250 μm. If required, said value can be reduced by micronisation or fine grinding.

An end-of-reaction crude product of preparation of a compound (III), typically having an assay value ranging between about 10 and 90% w/w, preferably between about 30% and 70% w/w, can then be subjected to the purification process according to the invention to obtain its crystalline form, in particular crystalline form A, with a chemical purity evaluated by HPLC greater than or equal to 95%, preferably greater than or equal to 98%.

In particular, a compound of formula (III) in crystalline form, in particular in Form A, obtained by the process according to the invention, contains a compound in the ido configuration of formula (V)

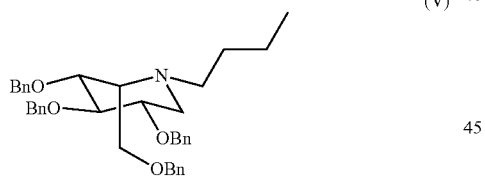

in quantities below 0.2%, preferably lower than 0.1%, calculated by HPLC.

A compound of formula (III), in crystalline form, in particular in crystalline form A, thus obtained, can be subjected to a debenzylation reaction to obtain miglustat with a high yield and purity, which can then be purified to obtain it in a crystalline form here designated as Form I.

The debenzylation reaction can be carried out according to known methods by removing the benzyl protecting group from the hydroxyl functions, preferably by catalytic hydrogenation.

According to a preferred aspect of the invention, miglustat can be obtained in crystalline form I by a purification process comprising:
 the formation of a solution of miglustat in a straight or branched $C_1$-$C_5$ alkanol, preferably methanol or ethanol;
 the addition of a straight or branched $C_3$-$C_7$, preferably acetone or methyl ethyl ketone;
 cooling of the mixture;
 and recovery of the solid.

A solution of miglustat in a $C_1$-$C_5$ alkanol can be formed at a temperature typically ranging between about 40 and 60° C.

The mixture can be cooled at a rate typically ranging between 0.1 and 5° C./min, preferably between 0.1 and 0.3° C./min, until its temperature ranges between ambient temperature and about −5° C. The mixture is maintained under stirring during said cooling and for a total of between about 2 and 20 hours thereafter.

The crystalline solid can be recovered by known techniques such as filtration or centrifugation, and optionally drying, such as stove-drying, at low pressure.

The product miglustat, namely N-butyl 1,5-dideoxy-1,5-imino-D-glucitol, obtained by the purification process according to the invention, is in crystalline form, designated here as Form I, having an XRPD spectrum, as illustrated in FIG. 3, wherein the main peaks (expressed in 2θ°) are found at 9.93, 11.82, 14.46, 15.84, 16.41, 17.76, 17.94, 19.41, 20.01, 20.79, 21.21, 22.14, 22.62, 23.40, 24.75, 26.04 and 30.27±0.2° in 2θ; and a DSC thermogram, as illustrated in FIG. 4, having an endothermic peak at 129-130° C. that indicates the fusion process.

Miglustat thus obtained, in particular in crystalline form I, has a chemical purity greater than or equal to 98%, preferably greater than or equal to 99%, calculated by HPLC.

A further subject of the present invention is therefore a method of preparing miglustat of formula (I), in particular in crystalline form I,

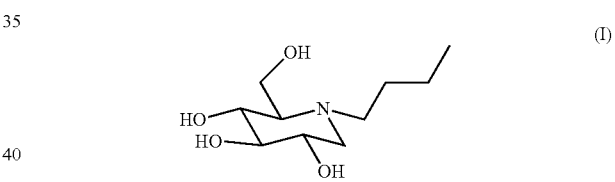

comprising the use, as starting material, of a compound of formula (III) in crystalline form, in particular in crystalline form A, as defined herein.

The product miglustat, as API (active pharmaceutical ingredient), obtained by the process according to the invention, in particular in crystalline form I, contains a compound in the ido configuration of formula (V)

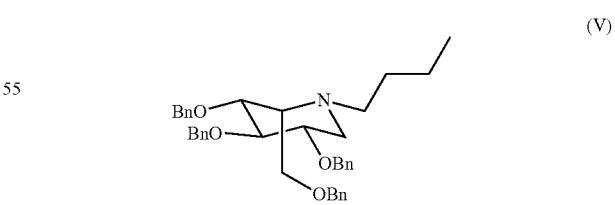

in quantities below 0.1%, preferably lower than 0.05%, calculated by HPLC.

A further subject of the invention is a pharmaceutical composition containing miglustat as active ingredient, in particular in crystalline form I, a compound in the ido configuration of formula (V)

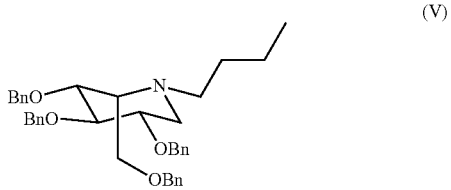 [SMILES: CCCCN1CC(OCc2ccccc2)C(OCc2ccccc2)C(OCc2ccccc2)C1COCc1ccccc1]

(V)

in quantities lower than 0.1%, preferably lower than 0.05%, calculated by HPLC, and a pharmaceutically acceptable carrier and/or diluent.

A further subject of the invention is a pharmaceutical composition containing miglustat as active ingredient, in particular in crystalline form I, and a pharmaceutically acceptable carrier and/or diluent.

The amount of active agent, in particular as crystalline form I, to be administered to a mammal, typically a human being, can typically range from about 70 to 150 mg, preferably 100 mg.

The preferably route of administration is orally in the form of capsules, tablets, syrups; although also parenteral administration can be used.

A pharmaceutical composition can be prepared according to known methods, for instance as disclosed in U.S. Pat. No. 5,472,969.

The size of the miglustat crystals, as obtainable by the process described above, in particular in crystalline form I, is characterised by a $D_{50}$ value of between about 25 and 250 µm. If required, said value can be reduced by micronisation or fine grinding.

The following examples illustrate the invention.

EXAMPLE 1

Synthesis of N-butyl 2,3,4,6-tetra-O-benzyl-1,5-dideoxy-1,5-imino-D-glucitol (III)

A solution of oxalyl chloride (99.8 g, 0.79 mol) in dichloromethane (300 mL) is cooled to −75° C., treated under inert atmosphere in sequence with a solution of DMSO (77.1 g, 0.99 mol) in dichloromethane (100 ml) added by slow dripping, and then, after about 1 h, with a solution obtained by dissolving 2,3,4,6-tetra-O-benzyl-D-glucitol, prepared as in Synthesis 1999, 571-573 (HPLC assay 94.5%, 105.9 g, 0.18 mol) in dichloromethane (100 mL), added by slow dripping. The reaction mixture is maintained under stirring at a temperature not exceeding 65° C., and treated after about 2 hours with triethylamine (187 g, 1.85 mol), added by slow dripping, maintaining the reaction mixture under stirring at a temperature not exceeding 50° C. for at least 4 hours. The end-of-reaction mixture is then added to a mixture maintained under stirring in an inert atmosphere at the temperature of 0° C., obtained by mixing n-butylamine (135 g, 1.84 mol), acetic acid (111 g, 1.85 mol), sodium sulphate (32.5 g, 0.51 mol) and sodium cyanoborohydride (31.7 g, 0.48 mol) in methanol (400 mL) The pH of the reaction mixture thus obtained is corrected by adding further acetic acid until a value of pH 6 is obtained, and the mixture is maintained under stirring at about 20° C. for 15 hours. The end-of-reaction mixture is then treated in sequence with a 20% aqueous solution of NaOH, 3M HCl to pH 6, an 11% solution of NaClO, a 10% solution of $Na_2SO_3$, a saturated solution of $NaHCO_3$, and finally with neutral water. The organic phase thus obtained is dried on anhydrous $Na_2SO_4$, filtered and concentrated at low pressure, to obtain an oily residue weighing about 120 g. The crude product thus obtained, analysed by HPLC, presents a ratio of about 4:1 between the product of formula (III) and the product of formula (V).

EXAMPLE 2

Crystallisation of N-butyl 2,3,4,6-tetra-O-benzyl-1,5-dideoxy-1,5-imino-D-glucitol (III)

The crude compound of formula (III), obtained as in Example 1, is dissolved in isopropanol (120 mL), and the resulting solution is cooled in an ice bath and treated with water (18 mL) The suspension obtained is maintained under stirring at about 20° C. for 15 hours, and then filtered through a Büchner funnel and the panel washed with isopropanol. The wet solid is stove-dried at the temperature of 50° C., under vacuum, to a constant weight, supplying 50 g of compound of formula (III) with high chemical purity, in crystalline form A, wherein the main peaks (expressed in 2θ°) are found at 4.83, 5.76, 6.96, 7.80, 13.08, 16.50, 17.97, 18.75, 19.14, 19.62. Said crystalline product presents a DSC thermogram as illustrated in FIG. 2, and a water content below 0.1%.

The compound of formula (III) can be recrystallised from isopropanol alone to obtain a compound of formula (III) with a purity, calculated by HPLC, exceeding 99%.

EXAMPLE 3

Synthesis of Miglustat of Formula (I)

A solution obtained by mixing N-butyl 2,3,4,6-tetra-O-benzyl-1,5-dideoxy-1,5-imino-D-glucitol of formula (III), obtained as in Example 2 (105.1 g, 0.17 mol) in methanol (500 mL) in the presence of 32% HCl (43.5 g), is treated with 16% Pd/C (10.2 g). The mixture is maintained under vigorous stirring under hydrogen atmosphere at 4 bars for about 4 hours, and then filtered through a perlite panel, and the solution obtained is concentrated at low pressure. The solid residue thus obtained is dissolved in water (100 mL), and the acid solution obtained is passed through a column on an ion-exchange resin activated in basic form (Amberlite IRA 900Cl). The fractions that tested positive to the ninhydrin assay were combined and concentrated at low pressure, obtaining 50 g of miglustat as an oily residue, having a chemical purity exceeding 98%, calculated by HPLC.

EXAMPLE 4

Crystallisation of Miglustat of Formula (I)

200 g of miglustat of formula (I) obtained as in Example 3 is diluted in methanol and treated by slow dripping, under stirring at about 20° C., with acetone. The suspension formed is maintained under stiffing at the same temperature for 5 hours and then filtered through a Büchner funnel, and the solid obtained is washed with acetone and dried at 50° C. under vacuum to a constant weight. 131 g of miglustat is obtained, with a purity calculated by HPLC exceeding 99.5%.

The product thus obtained is in crystalline form, designated here as Form I, having an XRPD spectrum, as illustrated in FIG. 3, wherein the main peaks (expressed in 2θ°) are found at 9.93, 11.82, 14.46, 15.84, 16.41, 17.76, 17.94, 19.41, 20.01, 20.79, 21.21, 22.14, 22.62, 23.40, 24.75, 26.04 and 30.27±0.2° in 2θ, as illustrated in FIG. 3; and a DSC thermogram having an endothermic peak at 129-130° C. which indicates the fusion process as illustrated in FIG. 4.

EXAMPLE 5

Crystallisation of Miglustat of Formula (I)

200 g of miglustat in the form of an oil, as obtained in Example 3, is diluted with 100 ml of methanol and placed under stirring at 50° C. Maintaining the temperature, 1000 ml of acetone is dripped in about 1 h. A white solid crystallises. At the end of the addition the mixture is cooled to ambient temperature in about 2 h, and left under stirring at that temperature for about 15 h. The solid is recovered by filtration through a Büchner filter and washed with acetone. The solid is dried at low pressure at about 50° C. until a constant mass is obtained. 131 g of crystalline miglustat is recovered.

The product thus obtained is in crystalline form, designated here as Form I, having an XRPD spectrum, as illustrated in FIG. 3, wherein the main peaks (expressed in 2θ°) are found at 9.93, 11.82, 14.46, 15.84, 16.41, 17.76, 17.94, 19.41, 20.01, 20.79, 21.21, 22.14, 22.62, 23.40, 24.75, 26.04 and 30.27±0.2° in 2θ, as illustrated in FIG. 3; and a DSC thermogram having an endothermic peak at 129-130° C. which indicates the fusion process as illustrated in FIG. 4.

The invention claimed is:

1. Miglustat, namely N-butyl 1,5-didesoxy-1,5-imino-D-glucitol in crystalline form, herein designated as Form I, having an XRPD spectrum as shown in FIG. 3, in which the most intense peaks (expressed in 2θ°) are to be found at 9.93, 11.82, 14.46, 15.84, 16.41, 17.76, 17.94, 19.41, 20.01, 20.79, 21.21, 22.14, 22.62, 23.40, 24.75, 26.04 and 30.27±0.2° in 2θ; and a DSC thermogram as shown in FIG. 4, having an endothermic peak at 129-130° C.

2. Miglustat in crystalline Form I, according to claim 1, having a chemical purity equal to or higher than 98%.

3. Miglustat in crystalline form I, according to claim 1, having a chemical purity equal to or higher than 99%.

4. Miglustat in crystalline Form I, according to claim 1, wherein the crystals have a $D_{50}$ value ranging from about 25 to about 250 μm.

5. Miglustat, as an API (Active Pharmaceutical Ingredient), in crystalline Form I, according to claim 1, containing a compound in ido configuration of formula (V)

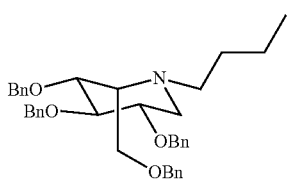

in an amount lower than 0.1%, determined by HPLC.

6. A process for preparing miglustat of formula (I) in crystalline Form I, as defined in claim 1,

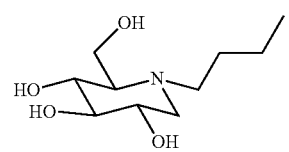

comprising the use, as starting product, of a compound of formula (III) in crystalline form, in particular in crystalline Form A,

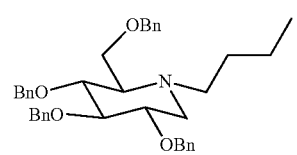

having an XRPD as shown in FIG. 1, wherein the most intense peaks (expressed in 2θ°) are to be found at 4.83, 5.76, 6.96, 7.80, 13.08, 16.50, 17.97, 18.75, 19.14, 19.62±0.2°.

7. A method for preparing miglustat in crystalline Form I, as defined in claim 1, by a purification process comprising:
obtaining a solution of miglustat in a straight or branched $C_1$-$C_5$ alkanol, preferably methanol or ethanol;
adding a straight or branched $C_3$-$C_7$ ketone, preferably acetone or methyl-ethyl ketone;
cooling the mixture; and
recovering the solid.

8. A pharmaceutical composition comprising miglustat as an active ingredient in crystalline Form I, as defined in claim 1, and a pharmaceutically acceptable carrier and/or diluent.

9. A pharmaceutical composition comprising miglustat as an active ingredient in crystalline Form I, as defined in claim 1, a compound in ido configuration of formula (V)

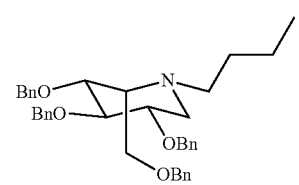

in an amount lower than 0.1%, determined by HPLC, and a pharmaceutically acceptable carrier and/or diluent.

10. A pharmaceutical composition according to claim 7, wherein the miglustat crystals have a $D_{50}$ value ranging from about 25 to about 250 μm.

11. A pharmaceutical composition according to claim 8 wherein the miglustat crystals have a $D_{50}$ value ranging from about 25 to about 250 μm.

* * * * *